US009775945B2

(12) United States Patent
Kaiser et al.

(10) Patent No.: US 9,775,945 B2
(45) Date of Patent: Oct. 3, 2017

(54) BOTTLE HOLDER FOR AN INJECTION DEVICE

(75) Inventors: Joerg Kaiser, Emmendingen (DE); Thomas Kranhold, Dessau (DE)

(73) Assignee: ULRICH GMBH & CO. KG, Ulm (DE)

( * ) Notice: Subject to any disclaimer, the term of this patent is extended or adjusted under 35 U.S.C. 154(b) by 1083 days.

(21) Appl. No.: 13/581,563

(22) PCT Filed: Feb. 8, 2011

(86) PCT No.: PCT/EP2011/051816
§ 371 (c)(1),
(2), (4) Date: Apr. 9, 2013

(87) PCT Pub. No.: WO2011/107327
PCT Pub. Date: Sep. 9, 2011

(65) Prior Publication Data
US 2013/0197361 A1    Aug. 1, 2013

(30) Foreign Application Priority Data

Mar. 1, 2010   (DE) ................. 10 2010 000 593

(51) Int. Cl.
*A61M 5/30* (2006.01)
*A61M 5/00* (2006.01)
*A61M 5/14* (2006.01)

(52) U.S. Cl.
CPC .......... *A61M 5/007* (2013.01); *A61M 5/1414* (2013.01); *A61M 5/1417* (2013.01)

(58) Field of Classification Search
CPC combination set(s) only.
See application file for complete search history.

(56) References Cited

U.S. PATENT DOCUMENTS 5,364,386 A   11/1994 Fukuoka et al.
5,989,237 A   11/1999 Fowles et al.
(Continued)

FOREIGN PATENT DOCUMENTS

DE   1934487 A1   1/1971
DE   19938078     2/2001
(Continued)

OTHER PUBLICATIONS

International Preliminary Report on Patentability published Sep. 3, 2012 for International Patent Application PCT/EP2011/051816.
(Continued)

*Primary Examiner* — Kari Rodriguez
*Assistant Examiner* — Sara Sass
(74) *Attorney, Agent, or Firm* — Paul D. Bianco; Gary S. Winer; Fleit Gibbons Gutman Bongini & Bianco PL

(57) ABSTRACT

The invention relates to a bottle holder (1) for an injection or infusion device, with a bottle receiver (2) for receiving a storage bottle, and with a spike secured on the bottle holder (1) for the purpose of punching an outlet opening into the storage bottle, or a holding means (3) for applying an exchangeable spike (4). In a development of such a bottle holder with which the infusion or injection device can be equipped as easily and as quickly as possible with a filled storage bottle, the invention proposes that the bottle receiver (2) is movable with respect to the spike (4) or with respect to the holding means (3) for the spike (4), and, when the bottle receiver (2) moves in the direction of the spike (4), a storage bottle arranged in the bottle receiver (2) is placed onto the spike (4) in such a way that the spike (4) punches an outlet opening into the storage bottle.

15 Claims, 9 Drawing Sheets (a)   (b)   (c)   (d)

(56) References Cited

U.S. PATENT DOCUMENTS

| | | | |
|---|---|---|---|
| 6,070,761 | A | 6/2000 | Bloom et al. |
| 6,071,270 | A | 6/2000 | Fowles et al. |
| 6,159,192 | A | 12/2000 | Fowles et al. |
| 6,464,105 | B1 | 10/2002 | Rolle et al. |
| 2005/0224133 | A1 | 10/2005 | Yui et al. |
| 2005/0273048 | A1* | 12/2005 | Landau .................. A61M 5/30 604/68 |
| 2008/0177126 | A1* | 7/2008 | Tate ...................... A61M 5/172 600/5 |
| 2009/0012464 | A1 | 1/2009 | Martin et al. |
| 2011/0092920 | A1 | 4/2011 | Martin et al. |

FOREIGN PATENT DOCUMENTS

| | | |
|---|---|---|
| DE | 20306395 U1 | 6/2003 |
| DE | 102010000593 | 9/2011 |
| EP | 1219283 A2 | 7/2002 |
| EP | 2011540 | 1/2009 |

OTHER PUBLICATIONS

Written Opinion of International Searching Authority dated May 15, 2012 for International Patent Application PCT/ EP2011/051816.
International Search Report published Sep. 9, 2011 for International Patent Application PCT/EP2011/051816.

\* cited by examiner

BOTTLE HOLDER FOR AN INJECTION DEVICE

FIELD OF THE INVENTION

The invention pertains to a bottle holder for an injection device.

BACKGROUND OF THE INVENTION

In the field of medical engineering, injection devices are used for injecting fluids into the body of a patient. Such injection devices may be used, for example, for administering contrast agents during imaging processes such as computer tomography procedures, ultrasonic examinations and magnetic resonance tomography (MRT) procedures. In this case, the fluids to be injected such as, e.g., different contrast agents and NaCl rinsing solutions are filled into storage bottles. The bottles containing the fluids to be injected are suspended, e.g., on the upper end of a floor stand that is usually supported on casters and connected to the injection device by means of a supply hose. The injection device comprises a pump such as, for example, a peristaltic pump, by means of which the fluids conveyed in the supply hoses are pumped into a patient hose that is intravenously connected to the patient. This arrangement proved disadvantageous because the supply hose between the storage bottle and the pump of the injection device needs to be ventilated when a new storage bottle is connected. Fluid may escape during this process and lead to soiling. In addition, the floor stand, on which the storage bottles are suspended, frequently does not have the required stability and may be inadvertently knocked over.

In order to eliminate these disadvantages, Utility Model DE 203 06 395 U1 proposes a contrast agent supply device that features at least one bottle receiver for receiving a contrast agent bottle, as well as a dosimeter pump for dosing the contrast agent, wherein the contrast agent can be conveyed from a contrast agent bottle placed into the bottle receiver to a patient hose that can be connected to a Braun's cannula with the aid of the dosimeter pump. A hollow spike for puncturing a pierceable seal of the contrast agent bottle is provided on the bottom of the bottle receiver or each bottle receiver. When a contrast agent bottle is inserted into the bottle receiver, the contrast agent bottle is opened by the puncturing spike such that the contrast agent can initially flow from the contrast agent bottle into the hollow puncturing spike and into a tank through a line that can be connected to the puncturing spike. The tank is connected to the dosimeter pump by means of connecting lines such that the dosimeter pump can take in the contrast agent from the tank and convey the contrast agent to the patient hose intravenously connected to the patient. In this contrast medium supply device, the bottle receiver or each bottle receiver is realized in the form of a cup-shaped bottle holder, the bottom region of which features a recess for receiving the top and the bottle neck of the contrast agent bottle. The hollow puncturing spike is arranged in the center of this recess. In order to load the contrast agent supply device with a full storage bottle, the operator needs to insert the storage bottle into the bottle receiver upside down (i.e., with the bottleneck pointing downward) and press the storage bottle on the puncturing spike until the puncturing spike has pierced an outlet opening into the contrast agent bottle.

This procedure is complicated, time-consuming and requires correspondingly skilled operating personnel. It also entails the risk, in particular, of the operator placing the contrast agent bottle on the puncturing spike in a noncentered fashion such that the puncturing spike cannot pierce an outlet opening through the sealing cap of the contrast agent bottle. This problem occurs, in particular, with smaller contrast agent bottles, the diameter of which is smaller than the inside diameter of the bottle receiver, because the inner wall of the cup-shaped bottle receiver cannot guide the contrast agent bottle during its placement on the puncturing spike in this case. The known arrangement furthermore proved disadvantageous because it is not possible to use larger contrast agent bottles, the diameter of which is greater than the inside diameter of the bottle receiver.

Another disadvantage of the known device manifests itself when a depleted contrast agent bottle is withdrawn from the bottle receiver. The bottle is pulled out of the bottle receiver vertically upward such that residual fluid can drip out of the outlet opening of the contrast agent bottle. Dripping residual fluid once again leads to soiling of the contrast agent supply device.

SUMMARY OF THE INVENTION

Based on these circumstances, the invention aims to disclose a bottle holder for an injection device that makes it possible to equip the injection device with a full storage bottle as easily and quickly as possible, wherein the bottle holder should be realized in such a way that it can receive various sizes of different storage bottles. The invention furthermore aims to disclose a bottle holder for an injection device, in which a depleted storage bottle can be remove from the bottle holder as easily as possible and without dripping.

The inventive bottle holder features a bottle receiver for receiving a storage bottle, as well as a puncturing spike that is fixed on the bottle holder and serves for piercing an outlet opening into the storage bottle or, alternatively, holding means for attaching an exchangeable puncturing spike. The bottle receiver can be respectively displaced relative to the puncturing spike that is rigidly arranged on the bottle holder or relative to the holding means for the exchangeable puncturing spike. In order to load a full storage bottle into an injection device that is equipped with such a bottle holder, the storage bottle is inserted into the bottle receiver upside down and pressed vertically downward. This causes the movable bottle receiver to move in the direction of the puncturing spike and places the storage bottle on the puncturing spike in such a way that it pierces an outlet opening into the storage bottle. Due to the guided movement of the bottle receiver relative to the puncturing spike, it is always ensured that the storage bottle and, in particular, its bottle neck is placed on the puncturing spike in a centered fashion such that the puncturing spike can pierce an outlet opening, e.g., through a cap or a thin membrane that seals the neck of the storage bottle.

The movement of the bottle receiver relative to the puncturing spike is preferably guided by means of a guide arrangement that is coupled to a spring. In this case, the bottle receiver can be displaced between an upper end position and a lower end position against the restoring force of a spring that is realized, in particular, in the form of a pressure spring. The bottle receiver can be advantageously fixed in the upper and/or in the lower end position by means of a locking mechanism. In its upper end position, the bottle receiver is ready to receive a new, full storage bottle. After inserting a full storage bottle into the bottle receiver, the bottle is pressed vertically downward such that the bottle receiver is moved toward the puncturing spike arranged thereunder, namely until the lower end position of the bottle receiver is reached. The puncturing spike has pierced an outlet opening into the storage bottle once the bottle receiver reaches the lower end position. The preferably hollow puncturing spike is connected to a supply line, through which the fluid can then be conveyed from the storage bottle into a pump of the injection device.

In order to allow the secure placement of storage bottles of various shapes and sizes into the bottle receiver of the inventive bottle holder, a funnel-shaped receiving element for inserting and holding the neck of a storage bottle therein is preferably provided on the inventive bottle holder. Furthermore, holding means that features flexible or pliable holding elements are preferably arranged on the bottle holder. The flexible holding elements at least partially encompass the storage bottle on its outer circumference and thusly fix the storage bottle in the bottle receiver. Due to the flexible or pliable design of the holding elements, they adapt to the size and the shape of the storage bottle and nonpositively adjoin the outer circumference of the storage bottle in order to fix this storage bottle in the bottle receiver. Consequently, it is also possible to fix bottles of different sizes and, in particular, different diameters in the bottle receiver.

The inventive bottle holder is preferably coupled to a housing part of the injection device such that it can be pivoted between a normal vertical position and a pivoted horizontal position. In this case, the pivoting mechanism is preferably realized such that the bottle holder can be pivoted relative to the housing part of the injection device in such a way in its lower end position that the storage bottle situated in the bottle receiver is transferred into an essentially horizontal position. In this horizontal position, the storage bottle can be pulled out of the bottle receiver without residual fluid dripping out of the outlet opening of the storage bottle.

In order to prevent the bottle holder from being inadvertently pivoted into its horizontal position, it is advantageous to provide a locking mechanism that locks the bottle holder in its vertical position. The bottle holder comprises an unlocking lever for disengaging the locking mechanism such that the bottle holder can subsequently be pivoted from its vertically lower end position into the horizontal position.

In order to ensure that the bottle receiver is in its upper end position, in which it can be once again loaded with a new storage bottle, when the bottle holder is pivoted back from its pivoted horizontal position into the normal vertical position, it is preferred to provide an automatic unlocking mechanism that automatically moves the bottle receiver into its upper end position when the bottle holder is pivoted back.

BRIEF DESCRIPTION OF THE DRAWINGS

Other advantages, as well as the handling of the inventive bottle holder and an injection device equipped with inventive bottle holders, result from the following description of one preferred exemplary embodiment that refers to the attached drawings. In these drawings:

FIG. 1a shows a detailed illustration of one of the three inventive bottle holders of the injection device according to FIG. 1a;

FIG. 5 shows sectional representations of the bottle holder according to FIG. 1a in different functional positions, wherein FIG. 5a shows the bottle holder in a lower vertical end position, FIG. 5c shows the bottle holder in a pivoted position and FIGS. 5b and 5d show the bottle holder in intermediate positions.

DETAILED DESCRIPTION OF THE INVENTION

Figure 1:
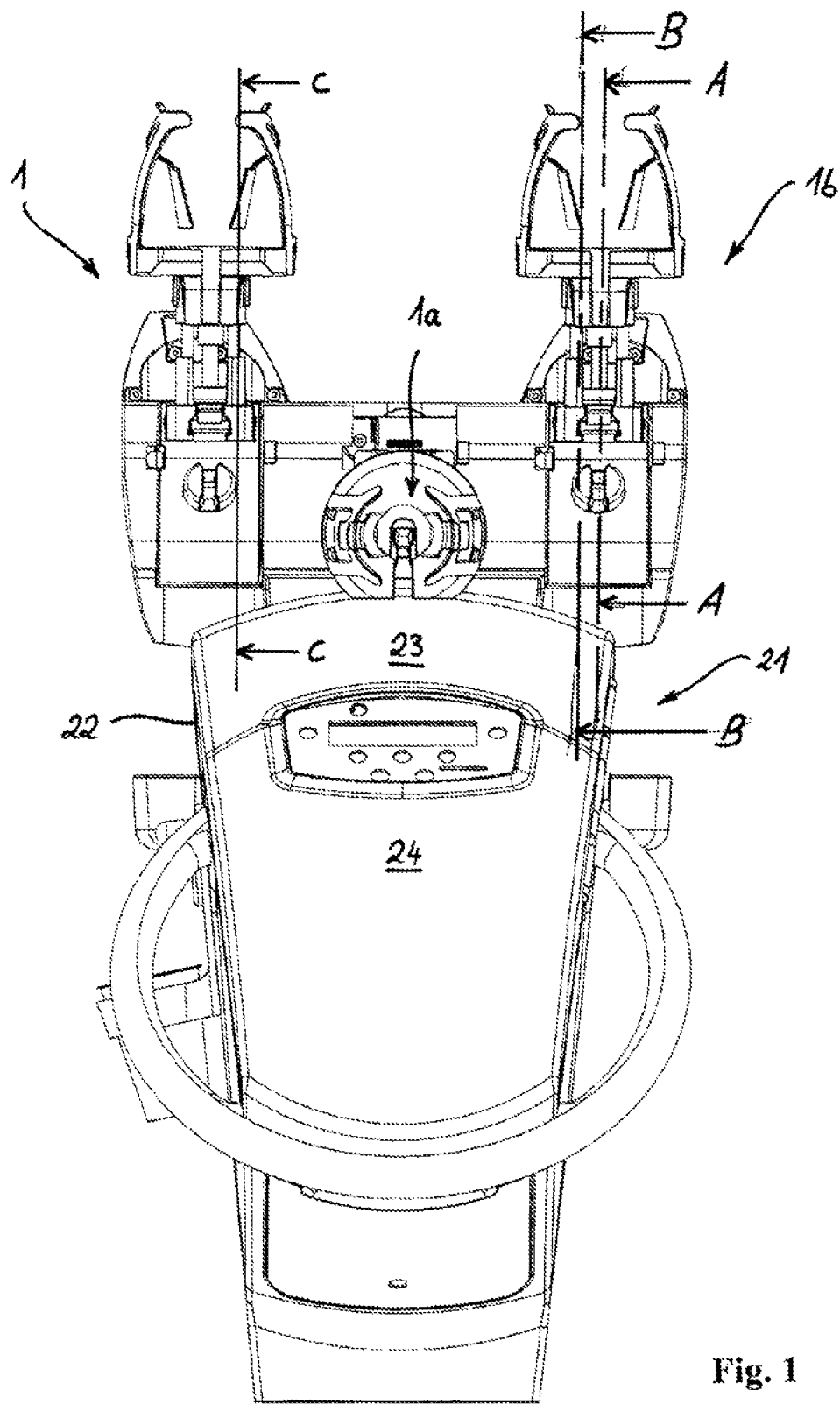
FIG. 1 shows a front view of an injection device with three inventive bottle holders.

FIG. 1 shows the injection head 21 of an injection device for injecting two different or identical contrast agents and a NaCl rinsing solution into the body of a patient, wherein the injection device features inventive bottle holders for receiving a total of three storage bottles for the two contrast agents and the NaCl rinsing solution. Such injection devices are used, for example, for injecting contrast agents during imaging processes such as computer tomography procedures, ultrasonic examinations and magnetic resonance tomography (MRT) procedures. The injection head 21 illustrated in FIG. 2 comprises an outer housing 22, in which a pump is arranged, preferably a peristaltic pump for conveying the contrast agents and the rinsing solution in a patient hose connected to the patient. A hose, in which the fluids to be injected are conveyed, is inserted into the peristaltic pump. The fluids to be injected are filled into (not-shown) storage bottles. In order to receive the storage bottles, the injection head 21 illustrated in FIG. 1 features a total of three bottle holders 1, 1a, 1b. The three bottle holders 1, 1a, 1b are arranged above a panel 23 of the injection head 21. The panel 23 can be closed with a cover 24. In the side view illustrated in FIG. 2, the cover 24 is shown in the closed position. In FIG. 1, the upper region of the panel 23 is visible through the preferably transparent cover 24. Channel-shaped recesses (that are covered by the cover 24 and therefore not visible) are provided in the upper region of the panel 23, wherein a branched hose arrangement (that is not graphically illustrated) can be inserted into said recesses. The hose arrangement may consist, in particular, of a hose arrangement of the type described in detail in EP 2 011 541 A2. This hose arrangement comprises a total of three supply hoses, namely a first supply hose for a first contrast agent, a second supply hose for a second contrast agent and a third supply hose for a rinsing solution (particularly NaCl). The three supply hoses are connected to the storage bottles for the contrast agents and the rinsing solution and clipped into the branch channels arranged in the upper region of the panel 23. The supply hoses arriving from the storage bottles converge in a junction element that is inserted into a circular recess. The junction element comprises an output hose that is inserted into the pump arranged in the housing 22 underneath the cover 24.

The three bottle holders 1, 1a, 1b illustrated in FIG. 1 are provided for receiving the storage bottles. The bottle holders are respectively designed identically. Details of the design of the bottle holders can be gathered from the detailed illustration in FIG. 1a, as well as the sectional representations in FIG. 3 and the perspective rear view in FIG. 4. The three bottle holders 1, 1a, 1b are respectively coupled to a housing part 20 of the injection head 21 in a pivoted fashion. Consequently, each of the three bottle holders 1, 1a and 1b can be pivoted between a normal vertical position and a horizontal position. In the illustration according to FIG. 1, the bottle holder 1 arranged on the left side and the bottle holder 1b arranged on the right side respectively are in their normal vertical position and the bottle holder 1a in the middle is in its horizontal position. A storage bottle can be inserted into the bottle holder and connected to a supply hose in the vertical position. After the storage bottle placed into the bottle holder has been connected to a supply hose, the bottle holder remains in its vertical position in order to withdraw the fluid from the storage bottle once the pump is running. The bottle holder can be pivoted into its horizontal position once the storage bottle has been depleted due to the operation of the pump. The depleted storage bottle can then be horizontally pulled out of the bottle holder in this horizontal position. Since the depleted storage bottle is pulled out of the bottle holder in the horizontal position, it is ensured that the depleted storage bottle is disconnected from the supply hose attached thereto without dripping. After the depleted storage bottle has been pulled out of the bottle holder, this bottle holder can be once again pivoted back into its normal vertical position. In the normal position, a full storage bottle can then be once again inserted into the bottle holder from above in the vertical direction.

Figure 1A:
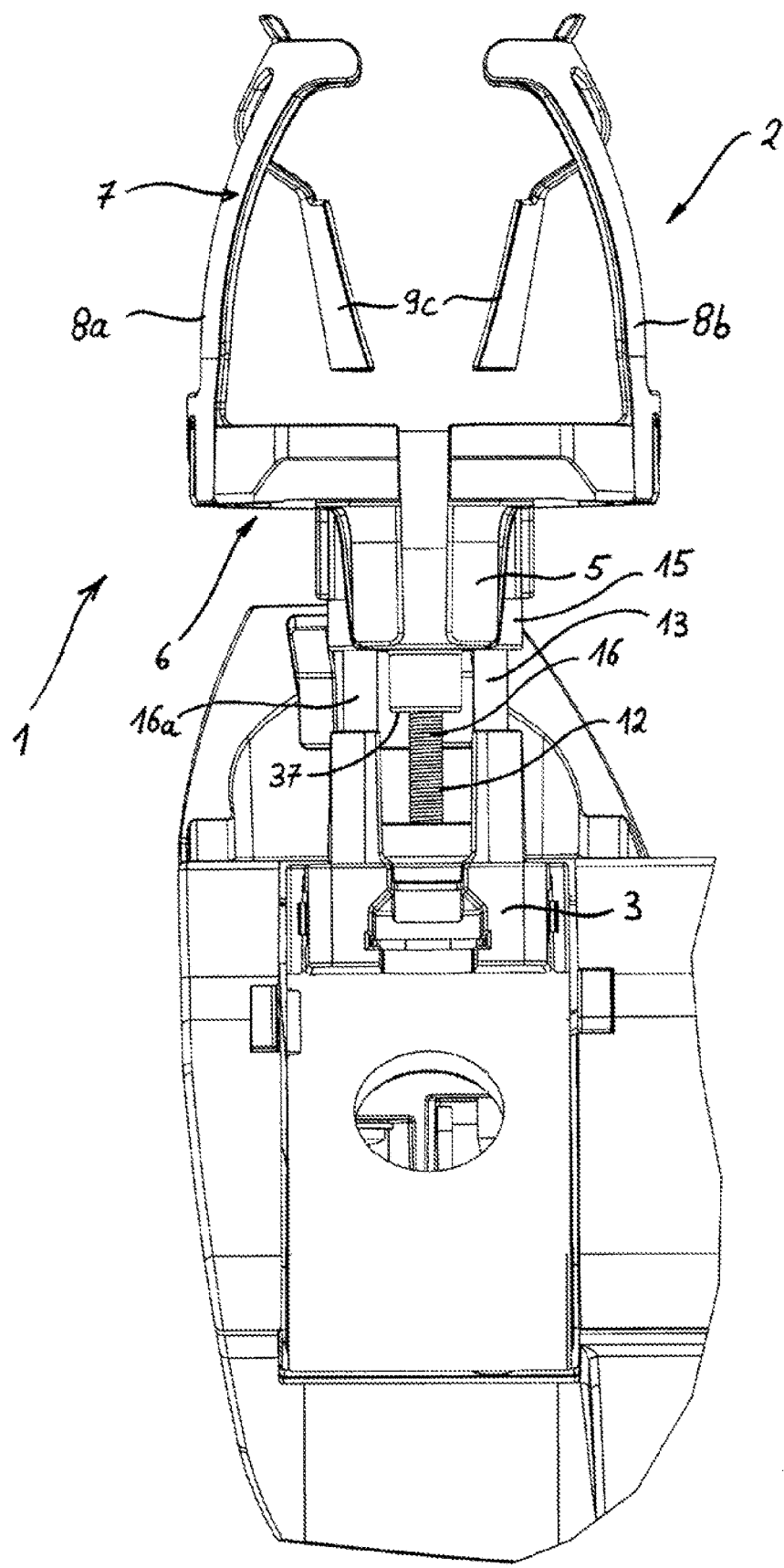
Figure 2:
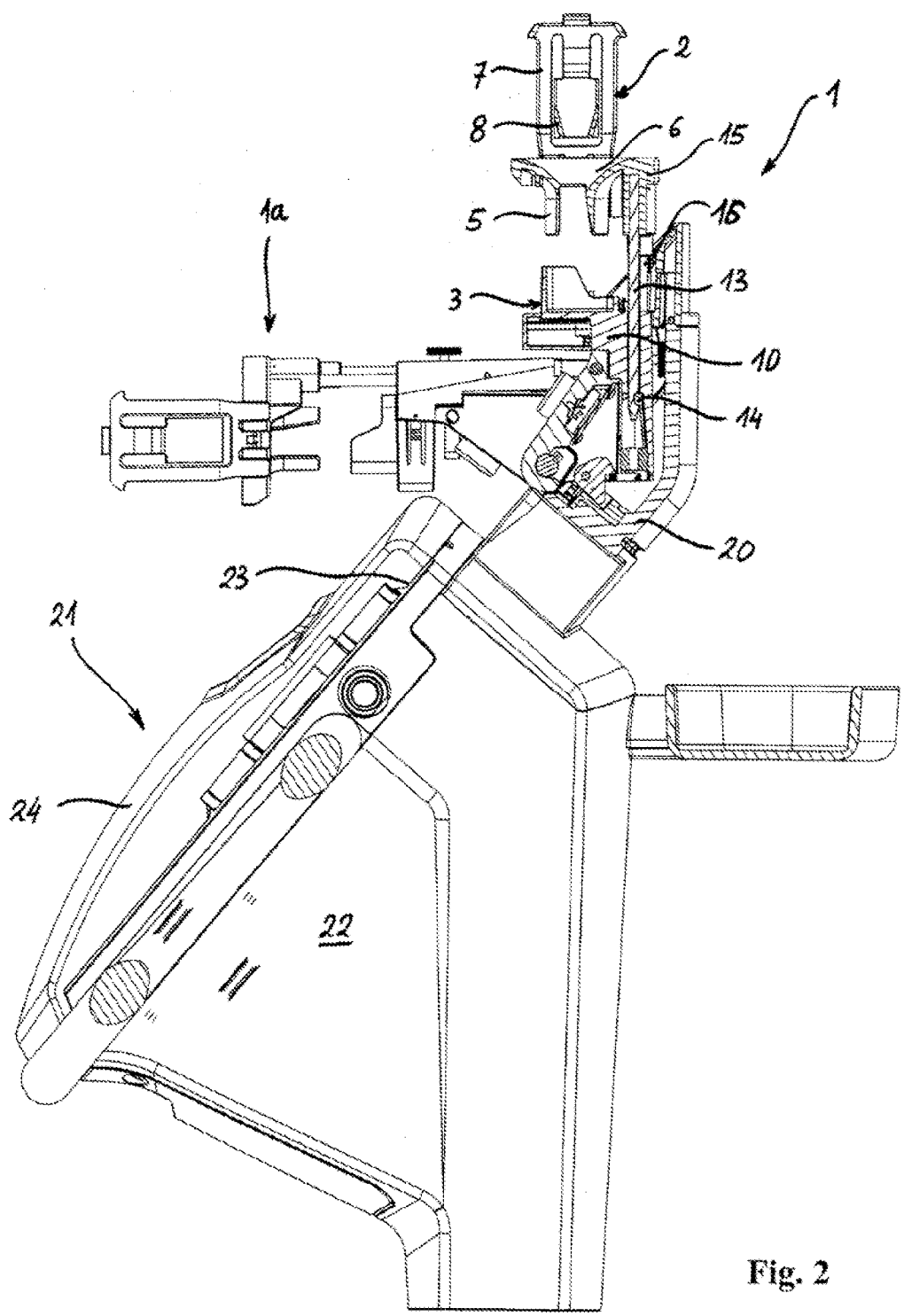
FIG. 2 shows a side view of the injection device according to FIG. 1.

In order to receive a storage bottle, each of the bottle holders 1 features a bottle receiver 2 (FIG. 1a). The bottle receiver 2 comprises a funnel-shaped receiving element 6, into which the bottle neck of a storage bottle can be inserted upside down (FIG. 2). The shape of the funnel-shaped receiving element 6 is advantageously adapted to the typical bottle shape of injection medium storage bottles or rinsing solution storage bottles, respectively. In order to ensure that the storage bottle is reliably held in the bottle holder, the bottle receiver 2 furthermore features holding means 7 that is arranged above the receiving element 6. The holding means 7 fixed on the receiving element features flexible holding elements 8. The flexible holding elements 8 encompass a storage bottle inserted into the bottle holder on its outer circumference in the central region or in the bottom region of the storage bottle such that the storage bottle is reliably fixed in the bottle holder and, in particular, in the receiving element 6. Due to these measures, storage bottles of different shapes and sizes can be securely fixed in the bottle receiver.

Figure 4:
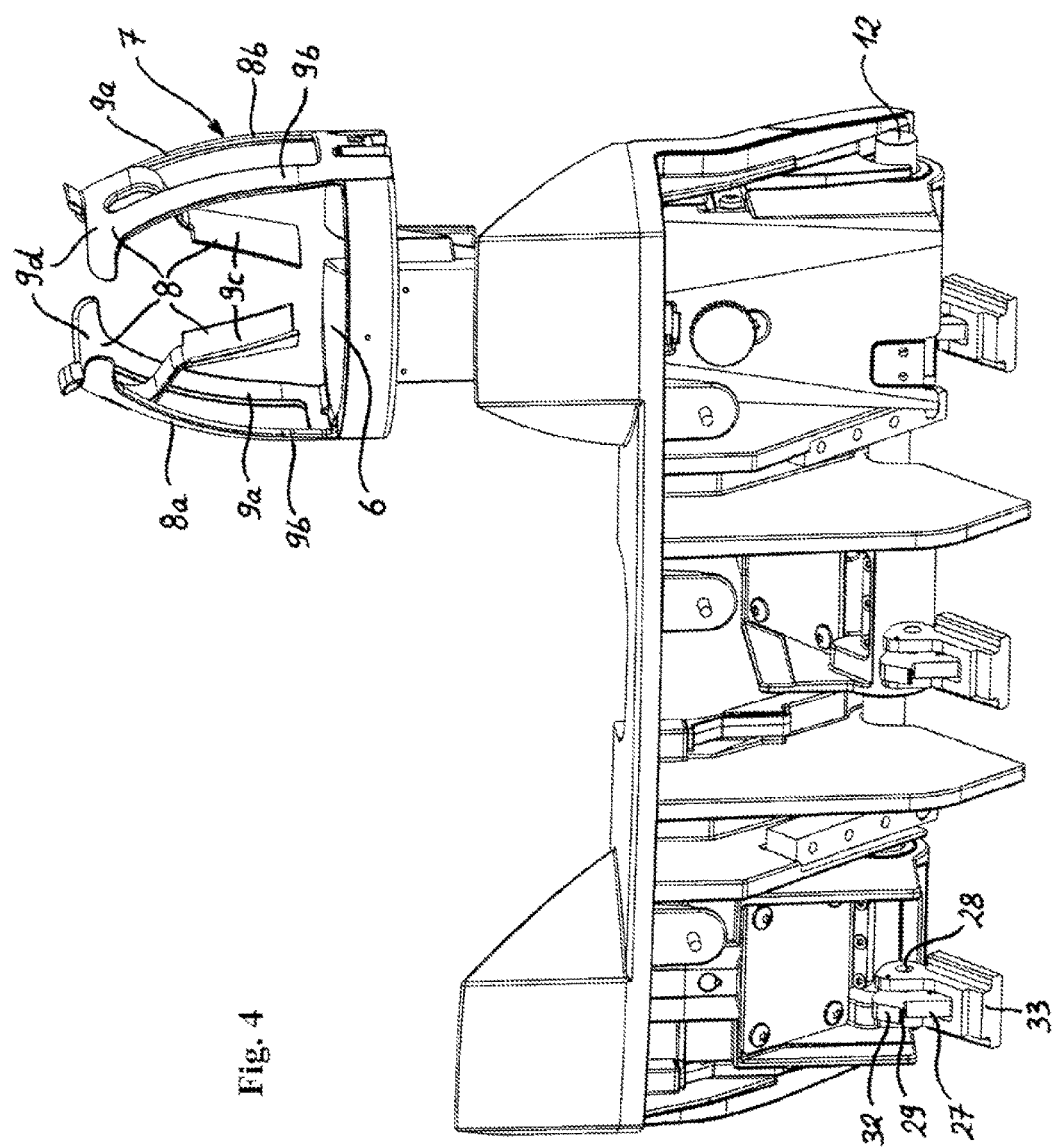
FIG. 4 shows a perspective rear view of the bottle holder according to FIG. 1.

The flexible holding elements 8 are preferably designed in such a way that they positively and nonpositively adjoin the outer circumference of the storage bottle. For this purpose, the holding means 7 features at least two holding elements 8a and 8b that are arranged on diametrically opposite locations referred to the insertable storage bottle (FIG. 1a and FIG. 4). Each of the identically designed holding elements 8a and 8b comprises a pair of first holding tabs 9a, 9b that are connected to one another by means of a connecting part 9d with the shape of a segment of a circle. A downwardly directed second holding tab 9c is arranged on the connecting part 9d. The second holding tab 9c extends between the two holding tabs 9a, 9b of the pair of first holding tabs and protrudes over the inner circumference of the connecting part 9d in the radial direction. Each holding element 8a, 8b is advantageously realized in one piece in the form of an injection-molded plastic part, i.e., the pair of first holding tabs 9a, 9b, the connecting part 9d and the second holding tab 9c are jointly molded in one piece in the form of an injection-molded part. Each holding element 8a, 8b is advantageously fixed on the funnel-shaped receiving element 6 in a detachable fashion by means of a latching or clamping mechanism. A splash guard 5 that is advantageously realized in one piece with the receiving element 6 in the form of an injection-molded plastic part is provided on the underside of the funnel-shaped receiving element 6.

Holding means 3 for attaching an exchangeable puncturing spike 4 is provided underneath the bottle receiver 2 (FIGS. 2 and 3). An inserted puncturing spike 4 is illustrated in the sectional representations according to FIG. 3. The holding means 3 features a guide rail or a guide groove 4. A holding part of a puncturing spike 4 that is realized with a complementary shape can be pushed into this guide rail or guide groove 4. The puncturing spike 4 advantageously consists of a hollow-cylindrical spike with a puncturing point, to which one end of a supply hose is connected, wherein the other end of said supply hose is connected to the junction element. As an alternative to this arrangement, the puncturing spike may also be permanently integrated into the bottle holder in that the puncturing spike is fixed on the holding means 3 or realized in one piece therewith. However, the described arrangement of a puncturing spike 4 that is detachably fixed on the holding means 3 is more practical because this design ensures that a used puncturing spike can be easily and quickly cleaned or exchanged, respectively.

In order to produce a connection between the supply hose and an initially closed storage bottle inserted into the bottle holder 1, a mechanism is provided that makes it possible to automatically pierce an outlet opening into the storage bottle by means of the puncturing spike. For this purpose, the bottle receiver 2 is realized such that it can be respectively moved relative to the puncturing spike 4 or relative to the holding means 3 for the puncturing spike. During a vertical movement of the bottle receiver 2 toward the puncturing spike, the storage bottle situated in the bottle receiver 2 is placed on the puncturing spike in such a way that the puncturing spike pierces an outlet opening into the storage bottle. Such storage bottles for contrast agents or rinsing solutions are usually sealed with a cap or a thin membrane that can be easily pierced by the puncturing spike. When the storage bottle is placed on the puncturing spike, the motion mechanism of the inventive bottle holder therefore automatically pierces an outlet opening into the cap or into the membrane of the storage bottle when the bottle receiver is manually pushed downward on the puncturing spike in the normal vertical position of the bottle holder. This merely requires that the operator presses the storage bottle inserted into the bottle holder 1 downward by exerting pressure upon the bottom thereof such that the bottle receiver 2 is also pushed downward in the direction of the puncturing spike.

Figure 3A:
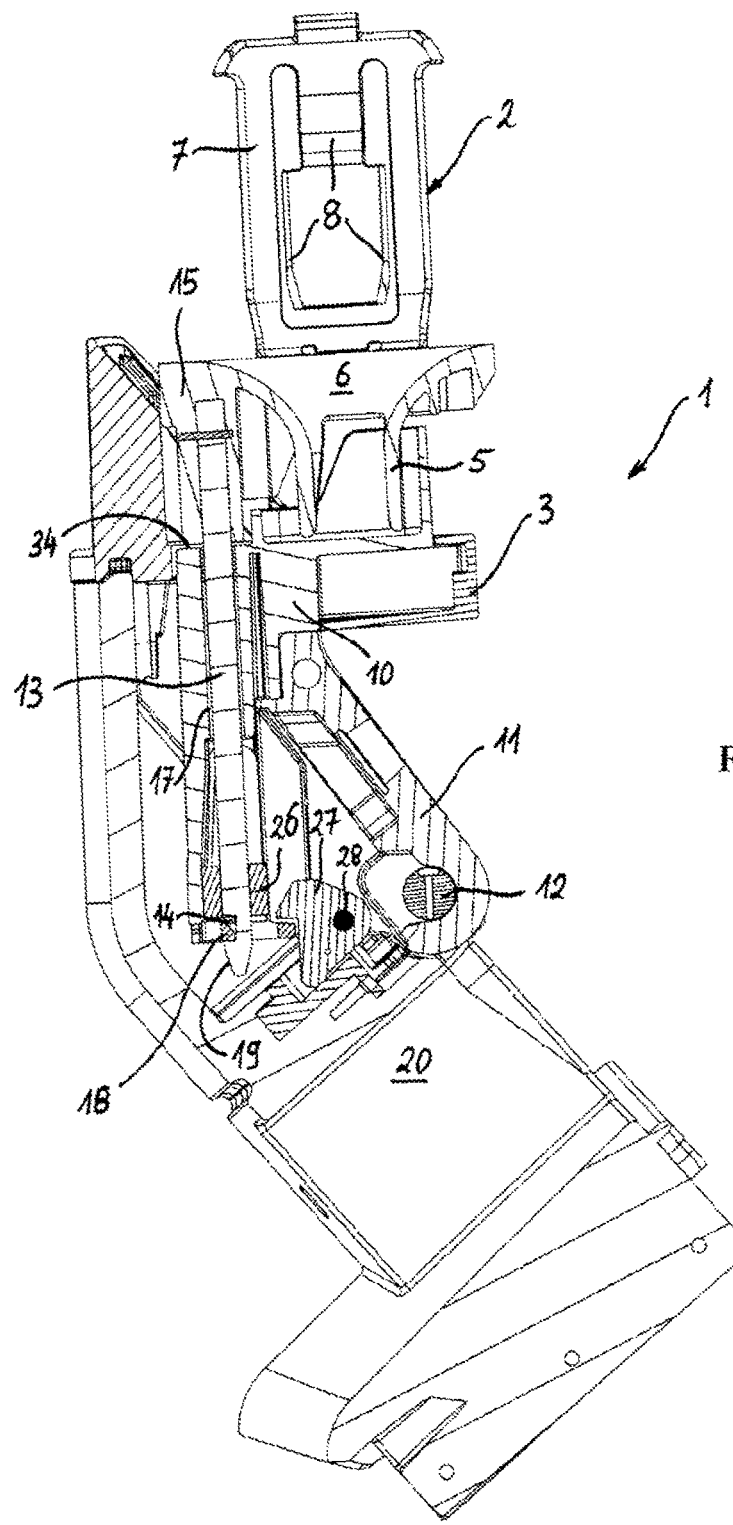
FIG. 3a shows a sectional representation of the left bottle holder according to FIG. 1 along the plane C-C in a normal vertical position.

The mechanism for respectively moving the bottle receiver 2 relative to the puncturing spike or the holding means 3 is illustrated in the sectional representations according to FIG. 3. FIG. 3a shows that each bottle holder 1 comprises a housing part 10, on which the holding means 3 for attaching an exchangeable puncturing spike 4 is fixed. A pivoted lever 11 is fixed on the housing part 10. The pivoted lever 11 is supported in a pivoting fashion on the housing part 20 of the injection head 21 by means of a pivot bearing 12. The mechanism for pivoting the bottle holder 1 relative to the housing part 20 from its (normal) vertical position illustrated in FIG. 3a into a horizontal position is described below.

A connecting part 15 featuring a vertical bore 36 is arranged on the underside of the funnel-shaped receiving element 6 and realized in one piece therewith. A guide rod 16 that is fixed on the connecting part 15 by means of a mounting bolt 35 protrudes into the aforementioned bore 36 (FIG. 3c). The guide rod 16 has a smaller diameter than the bore 36 and extends vertically downward up to the lower end 37 of the connecting part 15. A sleeve 38 is inserted into the housing part 10 and fixed therein. The sleeve 38 has a slightly smaller diameter than the bore 36 in the mounting part 15 and extends vertically upward from the housing part 10 up to the lower end 37 of the connecting part 15. The pressure spring 12 realized in the form of a coil spring is arranged in the sleeve 38, wherein the lower end of said coil spring rests on the bottom 39 of the sleeve 38. In its relaxed state (that is illustrated in FIG. 3c), the upper half of the pressure spring 12 encompasses the guide rod 16 and the upper end of the pressure spring 12 braces itself against a flange 40 on the guide rod 16. Consequently, the bottle receiver 2 can be displaced in the longitudinal direction of the guide rod 16 against the restoring force of the pressure spring 12. When pressure is exerted vertically downward upon the bottle receiver 2 and against the restoring force of the pressure spring 12, the pressure spring 12 is compressed and the lower region of the connecting part 15 is pushed over the sleeve 38, wherein the sleeve 38 engages into the bore 36 and the guide rod 16 (with the encompassing pressure spring 12) simultaneously engages into the sleeve 38. A guide arrangement that guides the movement of the bottle receiver 2 in the respective longitudinal direction of the sleeve 38 or the guide rod 16 is formed due to the cooperation of the guide rod 16, the mounting part 15 and the sleeve 38. However, it would also be conceivable to realize other embodiments of this guide arrangement, wherein the coil spring could, for example, be replaced with other spring elements such as, e.g., spiral springs or leaf springs.

A bolt 13 with a groove 14 arranged in the vicinity of its lower end is furthermore fixed on the mounting part 15 (FIG. 3a). The bolt 13 extends downward parallel to the guide element 16 and engages into a bore 17 in the housing part 10. In the normal vertical position of the bottle holder 1, the bottle receiver 2 can be displaced between an upper (vertical) end position and a lower (vertical) end position along the guide element 16 and against the restoring force of the pressure spring 12. In FIG. 2, the bottle receiver 2 is illustrated in its upper end position while the illustration according to FIG. 3 shows the bottle receiver 2 in its lower end position.

Figure 3B:
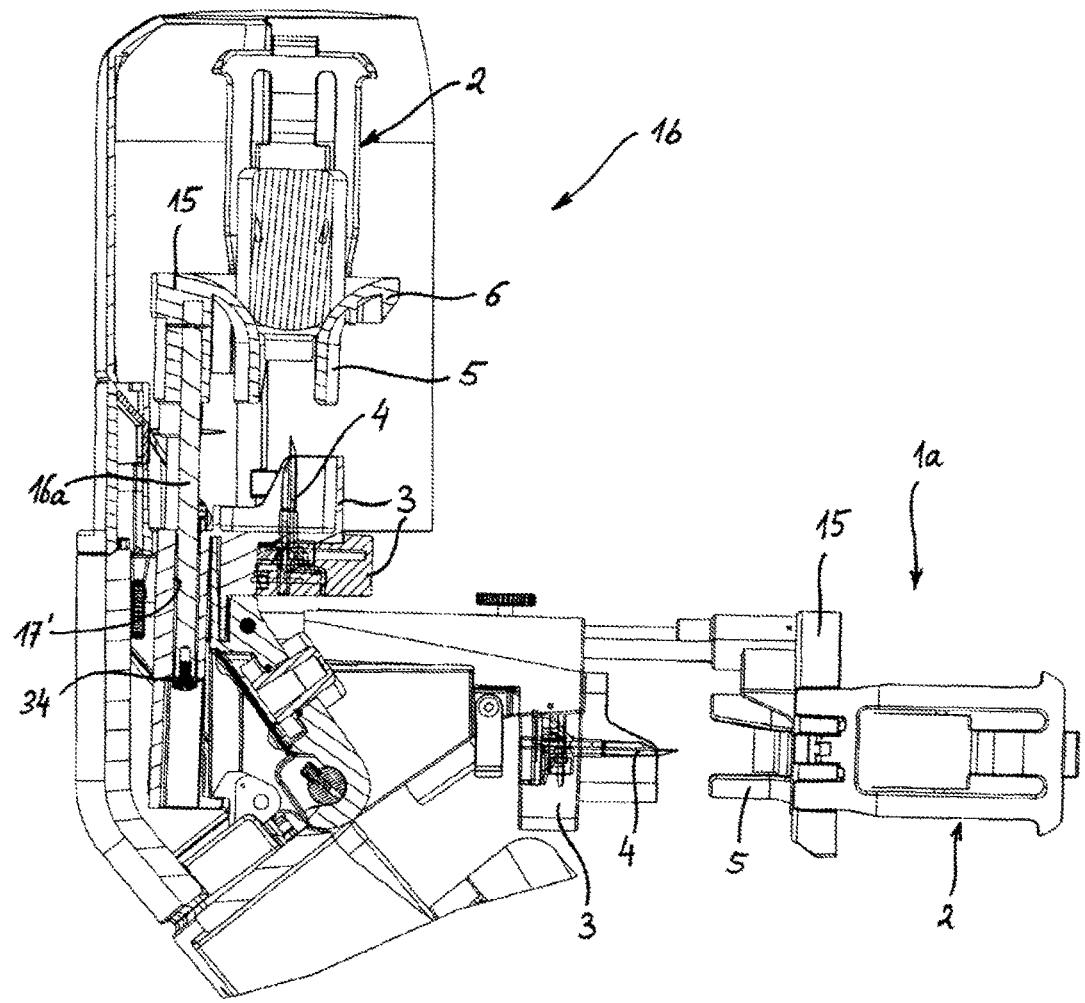
FIG. 3b shows a sectional representation of the right bottle holder according to FIG. 1 along the plane B-B in a normal vertical position.
Figure 3C:
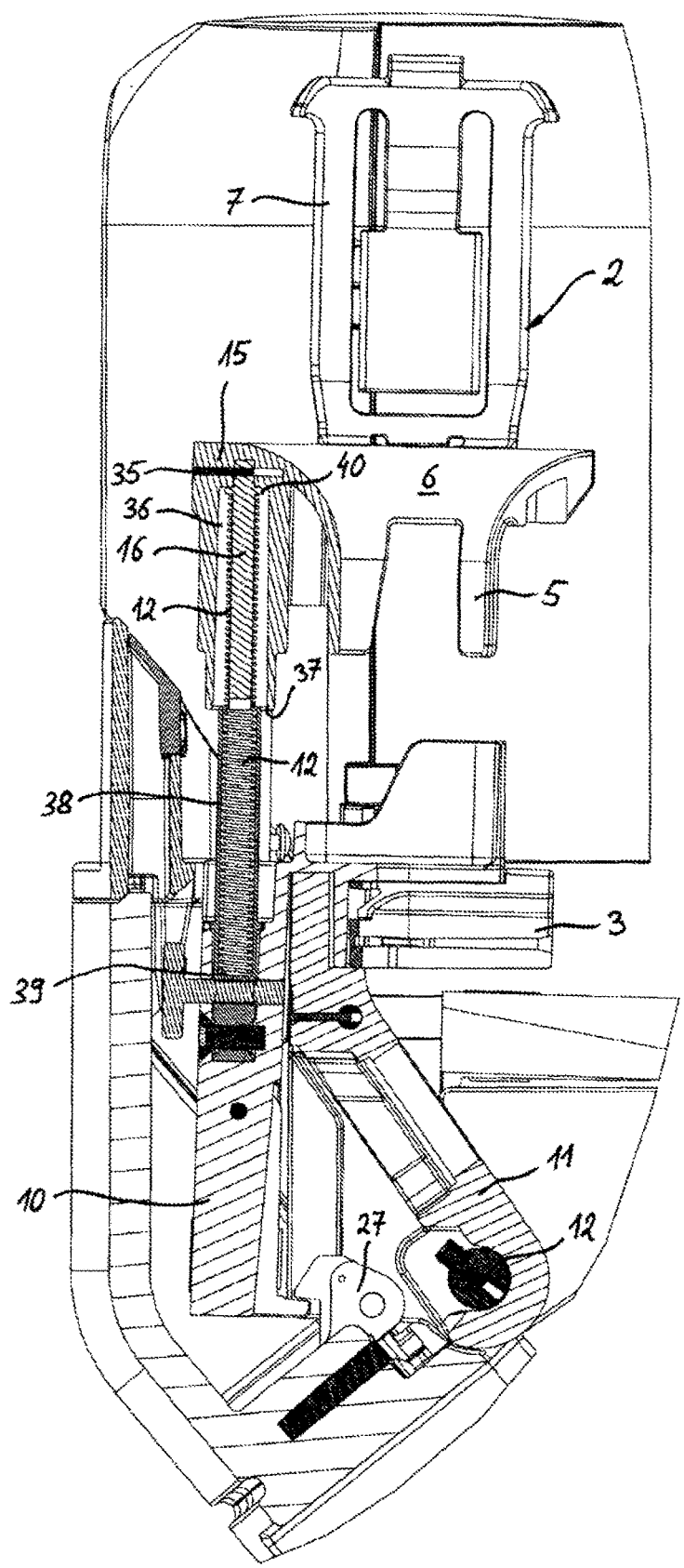
FIG. 3c shows a sectional representation of the right bottle holder according to FIG. 1 along the plane A-A in a normal vertical position.

According to the sectional representation in FIG. 3b, a second guide element in the form of a second guide rod 16a is provided in addition to the first guide element formed by the guide rod 16. This second guide rod 16a is realized similar to the bolt 13 and fixed on the mounting part 15 (FIG. 3b). The second guide rod 16a also extends downward parallel to the first guide rod 16 and engages into a bore 17' in the housing part 10. A flange 34 is screwed on the lower end of the second guide rod 16a. In the upper end position of the bottle receiver illustrated in FIG. 3b, the upper side of the flange 34 adjoins a step in the bore 17' and thusly fixes the bottle receiver 2 in its upper end position in connection with the restoring force of the pressure spring 12 that presses the bottle receiver 2 upward when the bottle holder is in its normal vertical position. The bottle receiver 2 can be pressed from its upper end position into the lower end position by exerting vertical pressure upon the bottle receiver from above against the restoring force of the pressure spring 12.

A latching mechanism is provided in the lower end position in order to fix the bottle receiver 2 in its lower end position. The latching mechanism for fixing the bottle receiver 2 in its lower end position comprises the bolt 13 that extends through the bore 17, as well as a latching tab 18 that engages into the groove 14 on the lower end of the bolt 13 when the bottle receiver 2 is in its lower end position. The lower end 19 of the bolt 13 is realized in a tapered fashion in order to actuate the latching mechanism. When the bottle receiver 2 is pressed downward from its upper end position, the bolt 13 fixed on the bottle receiver 2 moves through the bore 17 of the housing part 10 and engages into a sleeve 26 fixed on the housing part 10. A springable latching tab 18 is arranged on the underside of the sleeve 26. When the pointed end 19 is pushed through the sleeve 20, the pointed end 19 of the bolt 13 initially presses the springable latching tab 18 sideward until the latching tab engages into the groove 14 during the continued insertion of the bolt 13 and thusly locks the bolt 13, as well as the bottle receiver 2 fixed thereon by means of the receiving element 6, in this position (lower end position). During the movement of the bottle receiver 2 from its upper end position into the lower end position, the storage bottle in the bottle receiver 2 also moves toward the holding means 3 and the puncturing spike arranged therein such that the puncturing spike pierces an outlet opening into the storage bottle—as already described above. When the bottle receiver 2 is in its lower end position, the pump of the injection device can be started—after the storage bottle has been opened—in order to convey the liquid situated in the storage bottle.

Once the storage bottle has been depleted, the bottle holder 1 can be pivoted from its normal vertical position into the horizontal position by means of the pivoting mechanism in order to remove the depleted storage bottle. This can be achieved by unlocking an unlocking lever 11 (FIG. 1) that holds the pivoting mechanism in its locked position. For this purpose, the unlocking lever 11 is coupled to the pivot bearing 12, by means of which the pivoted lever 11 of the bottle holder 1 is coupled to the housing part 20 of the injection head 21.

Figure 5:
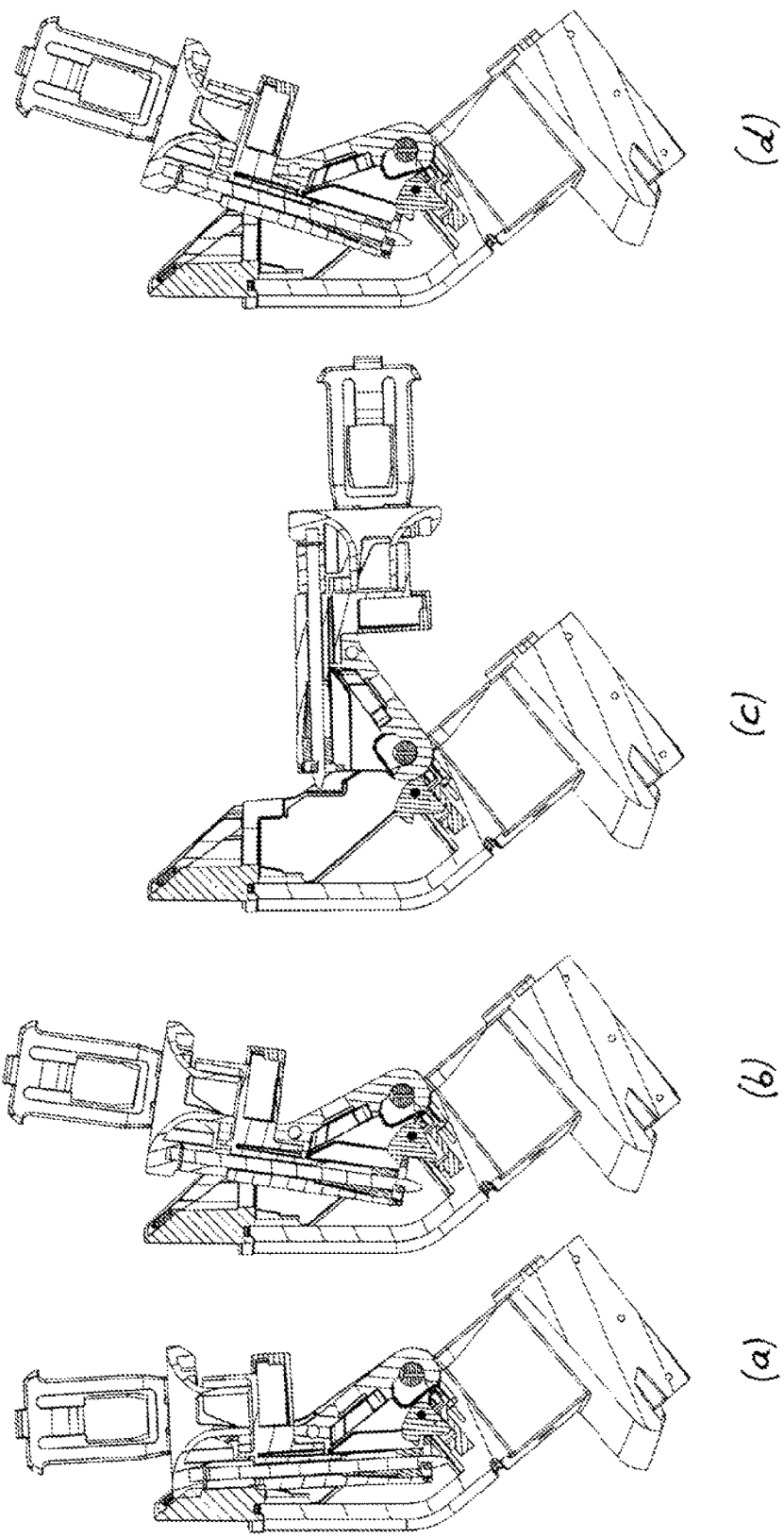

FIG. 5 shows different positions of the bottle holder 1 relative to the housing part 20 of the injection head 21 while the bottle holder 1 is pivoted from its normal vertical position (FIG. 5a) into an intermediate position (FIG. 5b) and ultimately into its pivoted horizontal position (FIG. 5c) and then once again pivoted back into its normal vertical position. In this respect, the illustration in FIG. 5a corresponds to the illustration in FIG. 3, in which the bottle holder 1 is in its normal vertical position and the bottle receiver 2 is in the lower end position. In this position, the bottle holder 1 can be pivoted into the horizontal position illustrated in FIG. 5c after the pivoting mechanism has been unlocked by actuating the unlocking lever 11. The bottle receiver 2 remains in its lower end position while the bottle holder 1 is pivoted from the vertical position into the pivoted horizontal position. This is illustrated in the sequence of pivoting positions shown in FIGS. 5a, 5b and 5c.

In order to ensure that the bottle receiver 2 is moved into its upper end position when the bottle holder 1 is pivoted back into the normal vertical position from its pivoted horizontal position, a mechanism is provided that automatically moves the bottle receiver 2 back into the upper end position from its lower end position while the bottle holder 1 is pivoted back into the normal vertical position from the pivoted horizontal position. This mechanism is illustrated in detail in the enlarged representation according to FIG. 6 and comprises a locking hook 27 that is fixed on a bolt 28. The bolt 28 is rotatably supported in a bearing part 33 that is fixed on the housing part 20 (FIG. 4). The locking hook 27 features a latching tab 29 that cooperates with a latching tab 30 that is arranged on the sleeve 26 and connected to the latching tab 18. In the lower end position of the bottle receiver 2 illustrated in FIG. 3, the latching tabs 29 and 30 lie on top of one another without engaging. When the bottle holder 1 is pivoted into its pivoted horizontal position, the latching tab 30 engages with the latching tab 29 and pulls the hook 27 upward (FIG. 5b). Due to these measures, the hook 27 is slightly raised and turned by turning the bolt 28 relative to the bearing part 33. Due to the rotational movement of the hook 27, the latching tabs 29 and 30 are once again disengaged and the bottle holder 1 can be additionally pivoted about the pivot bearing 12 until it reaches its pivoted horizontal position illustrated in FIG. 5c. In this pivoted horizontal position, the outer surface of the pivot bearing 11 rests on an abutment 31 of the housing part 20 and can no longer be pivoted further downward. In the pivoted horizontal position illustrated in FIG. 5c, the depleted storage bottle can be pulled out of the bottle receiver 2 without dripping.

Figure 6:
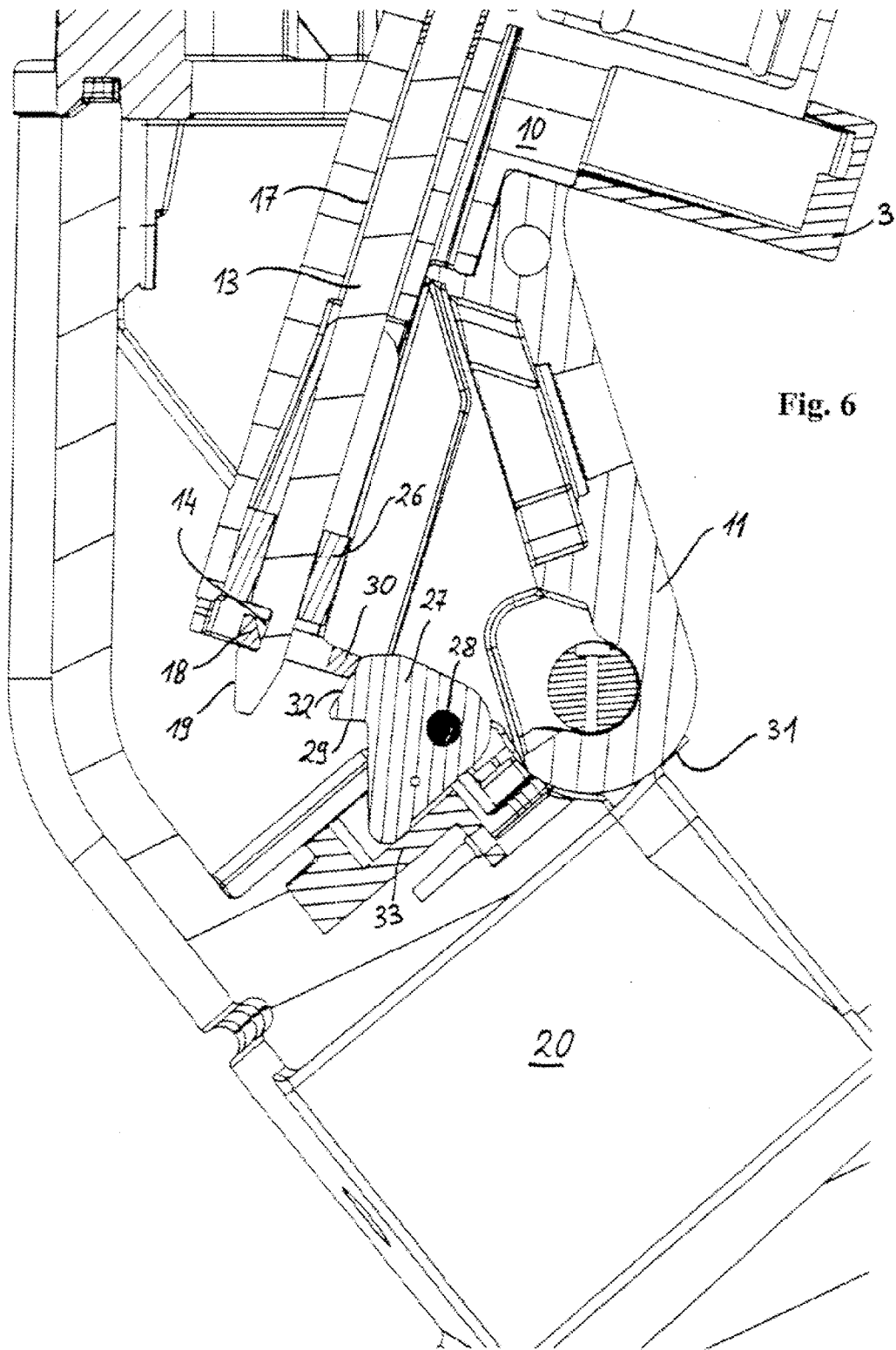
FIG. 6 shows a detailed illustration of the bottle holder according to FIG. 1a in the intermediate position illustrated in FIG. 5d.

When the bottle holder 1 is pivoted back into its normal vertical position (FIG. 5d) from its pivoted horizontal position (FIG. 5c), the latching tab 30 initially comes in contact with a guide surface 32 of the latching tab 29 in an intermediate position that is illustrated in FIGS. 5d and 6. As the bottle holder 1 is further pivoted back into its normal position, the latching tab 29 presses the latching tab 30 in the direction of the pivoting movement with its guide surface 32. The latching tab 30 is connected to the flexible latching tab 18 such that the latching tab 18 is pressed out of the groove 14 of the bolt 13 in the moving direction of the backward pivoting process. Due to these measures, the bolt 13 locked in the lower end position of the bottle receiver 2 is released and the bottle receiver 2 automatically moves back into its upper end position due to the restoring force of the pressure spring 12. Once the bottle holder has been completely pivoted back into its normal vertical position, the bottle receiver 2 has completely moved into its upper end position. This ensures that the bottle receiver 2 is in its upper end position once the bottle holder 1 has been pivoted back into its normal vertical position. In this normal vertical position, the bottle receiver can then be loaded with a new, full storage bottle. This is achieved by inserting a new storage bottle into the bottle receiver 2 and pressing the new storage bottle vertically downward in order to pierce an outlet opening into the storage bottle in the above-described fashion due to the movement of the bottle receiver 2 in the direction of the puncturing spike.

The invention is not limited to the described exemplary embodiment. For example, the inventive bottle holder is not only suitable for use in an injection device for injecting contrast agents, but also, for example, in infusion devices. In contrast to the described exemplary embodiment, it would also be possible to arrange less than three bottle holders on an injection or infusion device. Depending on the respective application, however, it would also be conceivable to provide more than three bottle holders of the inventive type on a corresponding device. It is also possible to utilize an inventive bottle holder for receiving a storage bottle together with a conventional bag holder for receiving a bag that contains a fluid to be injected.

The invention claimed is:

1. A device for injection or infusion of a liquid from one or more storage bottles, the device comprising:
a housing; and
at least one bottle holder, the bottle holder including:
a pivotable lever pivotally connected to the housing;
a puncturing spike for puncturing a bottle seal;
a spike holder connected to the pivotable lever the spike holder sized and dimensioned to releasably retain the spike;
a bottle receiver configured for holding a storage bottle; and
a guide arrangement attached to the pivotable lever;
wherein the bottle receiver is vertically movable in connection with the guide arrangement between an upper position, in which the storage bottle is not pierced by the puncturing spike, and a lower position, in which the puncturing spike pierces an outlet opening in the storage bottle; and
wherein the pivotable lever is pivotable from a vertical position into a horizontal position, wherein in the vertical position of the pivotable lever, the storage bottle is insertable into the bottle receiver when the bottle receiver is in the upper position, and the bottle receiver is movable toward the puncturing spike retained in the spike holder into the lower position to pierce the bottle with the puncturing spike, and by pivoting the pivotable lever into the horizontal position, the storage bottle is transferred to the horizontal position in which the storage bottle is pullable from the bottle receiver without releasing liquid from the bottle.

2. The device according to claim 1, wherein side surfaces of the bottle receiver form a funnel shape.

3. The device according to claim 1, wherein side surfaces are flexible and at least partially encompass an outer circumference of the storage bottle held in the bottle receiver.

4. The device according to claim 3, wherein the side surfaces include at least two opposed flexible holding elements.

5. The device according to claim 4, wherein each of the two opposed flexible holding elements includes holding tabs arranged thereon.

6. The device according to claim 5, wherein a pair of holding tabs is respectively connected to one another by a connecting part having a shape of a segment of a circle, and a further single holding tab is arranged on the connecting part and extends in a longitudinal direction of the storage bottle held in the bottle receiver between the two holding tabs of the pair of holding tabs.

7. The device according to claim 6, wherein the single holding tab protrudes over a circumference of the connecting part in a radial direction.

8. The device according to claim 1, further comprising a locking mechanism for fixing the bottle receiver in at least one of the upper position and the lower position.

9. The device according to claim 1, further comprising a pressure spring, wherein a connecting part and affixed bottle receiver are movable along the guide arrangement against a resistive force of the pressure spring.

10. The device according to claim 8, further comprising a latching tab attached to the housing and a cooperating latching tab connected to the pivotable lever, the latching tab and cooperating latching tab engageable for locking the pivotable lever in position.

11. The device according to claim 10, wherein the latching tab and cooperating latching tab automatically engage to lock the pivotable lever in the vertical position during pivoting movement from the horizontal position to the vertical position.

12. The device according to claim 1, wherein the liquid is a contrast agent for medical imaging.

13. The device according to claim 9, wherein the pressure spring is positioned to move the connecting part and affixed bottle receiver vertically after an inserted storage bottle has been pulled from the puncturing spike and the pivotable lever has been pivoted to the vertical position.

14. The device according to claim 13, further comprising a guiding surface connected to the housing, and a flexible latching tab connected to the pivotable lever and engageable with the guide arrangement as the connecting part is moved downwards, the guiding surface engaged with the flexible latching tab as the pivotable lever is moved from the horizontal position to the vertical position thereby causing the flexible latching tab to disengage the guide arrangement to enable the pressure spring to move the connecting part and affixed bottle receiver vertically.

15. The device according to claim 4, wherein the opposed flexible holding elements positively and non-positively adjoin the outer circumference of the storage bottle to fix the storage bottle in the bottle receiver.

* * * * *